United States Patent [19]

Soll et al.

[11] Patent Number: 4,918,165

[45] Date of Patent: Apr. 17, 1990

[54] MITOTIC INHIBITOR AND METHOD FOR PREVENTING POSTERIOR LENS CAPSULE OPACIFICATION AFTER EXTRACAPSULAR EXTRACTION

[75] Inventors: David B. Soll, Rydal; Thomsen J. Hansen, Havertown; Ihab Kamel, Drexel Hill, all of Pa.

[73] Assignees: Ophthalmic Research Corporation; Drexel University, both of Philadelphia, Pa.

[21] Appl. No.: 74,444

[22] Filed: Jul. 16, 1987

[51] Int. Cl.$^4$ ................... C07K 15/00; A61K 39/395
[52] U.S. Cl. .................................... 530/391; 530/389; 530/390; 514/885; 424/85.91; 424/422; 424/427
[58] Field of Search ..................... 530/389, 390, 391; 514/885; 424/85.91, 422, 427

[56] References Cited

U.S. PATENT DOCUMENTS

| 4,432,751 | 2/1984 | Emery et al. | 128/1 R |
| 4,515,794 | 5/1985 | Emery et al. | 514/249 |
| 4,699,784 | 10/1987 | Shih et al. | 530/391 |

OTHER PUBLICATIONS

Carper et al., *Dev. Biol.*, 113, 1986, pp. 104–109.
Matthay et al, *Cancer Res.*, 46, 1986, pp. 4904–4910.
Endo et al, *Cancer Res.*, 47, 1987, pp. 1076–1080.
Garnett et al, *Cancer Res.*, 46, 1986, pp. 2407–2412.
Emery et al., CA, vol. 99, 1983, #193053u.
Robinson et al., "Cell-Directed Anti-Metabolites: Alternative Syntheses of Cytotoxic Methotrexate-Containing Macromolecules," *Biochemical Society Transactions*, 1:722–726 (1973).
Hattori et al., "Specific Effects of Methotrexate Bound to the Antibodies Against hCG and Placental Alkaline Phosphatase to the Cultured Human Choriocarcinoma Cells," *Acta Obst Gynaec JPN*, 35:33–40 (1983).
Kulkarni et al., "Covalent Binding of Methotrexate to Immunoglobulins and the Effect of Antibody-Linked Drug on Tumor Growth in Vivo," *Cancer Research*, 41:2700–2706 (1981).
Burstein et al., "Chemotheraphy of Murine Ovarian Carcinoma by Methotrexate-Antibody Conjugates," *J. of Medicinal Chemistry*, 20:950–951 (1977).
Jacobs et al., "Discussion Paper: 'Some Biochemical and Pharmacologic Properties of Amethopterin-Albumin,'" *Ann. N.Y. Acad. Sci.*, 186:284–286 (1971).
Garnett et al., "Preparation and Properties of a Drug--Carrier-Antibody Conjugate Showing Selective Antibody-Directed Cytotoxicity in Vitro," *Int. J. Cancer*, 31:661–670 (1983).

*Primary Examiner*—Garnette D. Draper
*Attorney, Agent, or Firm*—Panitch Schwarze Jacobs & Nadel

[57] ABSTRACT

A conjugated cytotoxin is provided for preventing posterior lens capsule opacification (after-cataract) after extracapsular extraction. Preferably, the mitotic inhibitor of lens epithelial cells comprises a conjugate containing methotrexate which is covalently linked to an antibody, such as anticollagen, in approximately a molar ratio of 1:1 to 10:1. The mitotic conjugate may be instilled in the anterior or posterior chamber of the eye, preferably immediately after the lens has been removed, or coated onto an intraocular lens prior to insertion onto the posterior lens capsule. Similar conjugates may be attached to other artificial materials in the body to fight fibroblast proliferation.

9 Claims, No Drawings

MITOTIC INHIBITOR AND METHOD FOR PREVENTING POSTERIOR LENS CAPSULE OPACIFICATION AFTER EXTRACAPSULAR EXTRACTION

FIELD OF THE INVENTION

The present invention relates to an improved method and material for preventing opacification of the posterior capsule (after-cataract) after extracapsular cataract surgery. More particularly, the invention relates to a method and means for targeting a cytotoxic drug to inhibit the growth of lens epithelial cells and/or fibroblasts or other cells on the lens capsule.

BACKGROUND OF THE INVENTION

Extracapsular lens extraction has become the method of choice for removing cataracts. The major medical advantages of this technique over intracapsular extraction are lower incidence of aphakic cystoid macular edema and retinal detachment. Extracapsular extraction is also required for implantation of posterior chamber type intraocular lenses which are now considered to be the lenses of choice in most cases.

A disadvantage of extracapsular cataract extraction is the high incidence of posterior lens capsule opacification, often called after-cataract, which can occur in up to 50% of cases within three years after surgery. After-cataract can be treated by additional surgical procedures (e.g., posterior capsulotomy, repolishing of the posterior lens capsule, or disruption of capsule by infrared energy from a neodymium YAG laser) to obtain good vision. There are complications associated with all types of capsulotomy. These include cystoid macular edema, retinal detachment, and transient or permanent glaucoma.

After-cataract is caused by proliferation of equatorial and anterior capsule lens epithelial cells which remain after extracapsular lens extraction. These cells proliferate to cause Sommerling rings, and along with fibroblasts which also deposit and occur on the posterior capsule, cause opacification of the posterior capsule, which interferes with vision. Prevention of after-cataract would be preferable to treatment, and could be achieved by physically or chemically destroying the lens cells at the time of the original cataract extraction.

In animal experiments, cytotoxic drugs administered during surgery or implantation have been investigated as a means of inhibiting the growth of lens epithelial cells. An example of such a drug is methotrexate (MTX), as described in U.S. Pat. No. 4,515,794. MTX kills dividing cells preferentially, though not exclusively, and is used in cancer chemotherapy.

As described in the above patent, MTX has been used as a mitotic inhibitor by instilling a solution containing a specific concentration of methotrexate into the anterior chamber of the eye after lens removal. Furthermore, the solution containing MTX is osmotically balanced to provide minimal effective dosage when instilled into the anterior chamber of the eye, thereby inhibiting subcapsular epithelial growth.

However, because MTX is not specific as to the type of cell that it kills, serious side effects can occur. Moreover, epitheliel cells must divide for MTX to exert its cytotoxic effect. The drug should therefore remain in the eye at least through the generation time of the lens epithelial cells. While these cells normally divide very slowly and only at the equator, division is stimulated by injury, such as would occur during surgery, occurring within 48 hours. Mitotic inhibitors comprised simply of solutions of methotrexate or other cytotoxins which are instilled in the aqueous fluid of the eye would be continually diluted by inflow of aqueous fluid which is renewed with a half time of about three hours. This dilution in turn decreases the ability of the drug to inhibit growth of the epithelial cells which remain after lens extraction.

SUMMARY OF THE INVENTION

The present invention relates to a mitotic inhibitor effective to inhibit lens epithelial cell growth and fibroblastic proliferation by instilling into the anterior or posterior chamber of the eye during or immediately following cataract surgery a cytotoxic agent coupled with means to target the cytotoxic agent to particular cell types. Preferably, this is accomplished by coupling methotrexate with an antibody, such as anticollagen, thus yielding a conjugate in which the molar ratio of methotrexate to anticollagen is about 1:1 to 10:1.

Targeting of the MTX will allow for a much lower concentration of MTX (compared to the use of free MTX as in U.S. Pat. No. 4,515,794) to be instilled into the eye's anterior or posterior chamber, thus decreasing the possibility of the patient experiencing harmful side effects. Furthermore, a larger concentration of MTX can also be used, as needed, with the likelihood of side effects occurring also being lessened due to the targeting of the MTX specifically to lens epithelial cells.

DESCRIPTION OF PREFERRED EMBODIMENTS

According to the present invention, the prevention of after-cataract is improved by coupling to the cytotoxic agent for destroying lens capsule cells and fibroblasts an antibody which will target the cytotoxin to the particular area of the eye desired and retain the cytotoxin in this area of the eye for sufficient time to effectively kill the dividing cells which cause the lens capsule opacification. Although other cytotoxins may be used in accordance with the teachings of the present invention, the most preferred cytotoxin is methotrexate, which has been demonstrated in U.S. Pat. No. 4,515,794 to be effective in destroying the epithelial cells of the lens capsule which remain after cataract surgery. Methotrexate is well known in the art and is commercially available, for example, from Sigma Corporation.

In order to target the cytotoxin to the site where the cytotoxin will kill the desired epithelial cells, fibroblasts or other undesirable cells, the cytotoxin is linked or conjugated to an antibody which will attach itself to a particular area of the eye. The antibody may be one which is specific to the cells sought to be destroyed, or an antibody which is specific to the lens capsule may be used.

According to the present invention, it has been found that antibody to human basement membrane collagen, the most common collagen in the eye, (anticollagen) is effective in targeting the cytotoxin to the lens capsule for destruction of lens epithelial cells. Anticollagen is known in the art and commercially available, for example, from Australian Monoclonal Development of Artarmon, N.S.W., Australia. This is a mouse monoclonal IgG, as described, for example, in Hancock, W. W., Kraft, N., and Atkins, R. C., "Production of Monoclonal Antibodies to Fibronectin, Type IV Collagen and other Antigens of the Human Glomerulus," *Pathology* 16:197 (1984).

While the antibody and cytotoxin may be linked or conjugated by a number of methods, it is preferred that they be linked by a covalent bond, preferably using the water soluble carbodiimide EDCI as a condensing agent. This method is known in the art, as described and referenced in Preparation Example 1 below.

A molar ratio of cytotoxin to antibody in the range of about 1:1 to 10:1 appears to be satisfactory. Although optimum concentrations of the cytotoxin and antibody in the conjugate have not been determined, it has been found in tests to date that a molar ratio of methotrexate to anticollagen of about 2.5:1 produces satisfactory results. It is believed that effective conjugates may be produced by using other molar ratios, other cytotoxins, or by using an antibody specific to other lens cells besides lens capsule.

According to the method of the invention, the conjugate may be instilled in the anterior or posterior chamber of the eye during or after extracapsular extraction, in the same manner as the instillation of methotrexate or other cytotoxin alone, as described in U.S. Pat. No. 4,515,794. The significant difference, however, is that whereas the methotrexate or other cytotoxin alone is continually diluted by the inflow of aqueous fluids in the eye and remains for only a very short time, the targeted cytotoxin using the conjugates of the present invention will enable the cytotoxin to remain in the eye for much longer periods to allow the continued destruction of lens epithelial cells as they are generated after surgery.

The MTX-anticollagen conjugate according to the invention retains both antimetabolic and antibody activity, as shown through biochemical measurements. It is an effective inhibitor of the outgrowth of lens epithelial cells in vitro, and initial animal experiments support the possibility that the conjugate would be effective in vivo. The effects seen were due specifically to the conjugate, since free MTX, free anticollagen, a non-specific conjugate, or buffer failed to produce the desired results. As with antibody targeting of MTX to cancer cells in vitro (see Kulkarni et al. above) free MTX and free anticollagen somewhat inhibited cell outgrowth, but did not completely suppress it as did the conjugate.

An alternative method according to the present invention comprises attaching the cytotoxin/antibody conjugates to artificial lenses, such as intraocular lenses. The conjugate is attached to the lens prior to insertion of the lens during surgery. The cytotoxin is then available for killing epithelial lens cells after the surgery.

For example, as described more fully below, a covalent conjugate of MTX with bovine serum albumin may be attached to a polymethyl methacrylate (PMMA) which has been plasma treated with ethylene diamine using glutaraldehyde (GA) to attach the conjugate to the treated PMMA lens. Other coating and attachment methods will be evident to those skilled in the art. Still further, the method of the invention may be used to attach cytotoxin/antibody conjugates to the other artificial materials in other areas of the body, such as attachment to shunts to fight the buildup of fibroblasts which may clog blood vessels.

The invention will now be described in more detail with reference to the following specific, non-limiting examples:

PREPARATION EXAMPLE 1

The conjugate was prepared by covalently linking antibodies (anticollagen and antialbumin) with methotrexate using the water-soluble 1-ethyl-3-(3-dimethylaminopropyl) carbodiimide (ECDI) as a condensing agent. Both unlabelled and $^3$HMTX labelled conjugates were prepared. The labelled material was 3'-5'-7-3HMTX with a specific activity of 33.7 mCi/mg (15.3 Ci/mmol) obtained from Amersham. The procedure followed that of Kulkarni, P. N., Blair, A. H. and Ghose, T. I., "Covalent Binding of Methotrexate to Immunoglobulins and the Effect of Antibody-Linked Drug on Tumor Growth In Vivo," *Cancer Res.* 41:2700 (1981). Ten mg MTX and 2 mg ECDI were mixed in 1.5 ml of buffer (0.01M sodium phosphate buffer, pH 7.5, all references to buffer refer to this). After 10 minutes, the mixture was centrifuged and 150 ul of the supernatant containing 1 mg MTX, were removed and mixed with 0.5 mg of antibody in a volume of 0.5 ml. Premixing the MTX and ECDI provided much better protein recovery than when all three reagents were mixed together. This was shaken in the dark for four hours, and the conjugate separated from unbound MTX by gel filtration on a 1 cm×25 cm column of BioGelP6, using buffer for elution. Column fractions were analyzed by absorbance at 280 nm and 370 nm, by inhibition of the enzyme dihydrofolate reductase and, when tritium labelled MTX was used, by scintillation counting.

Antibody activity in the conjugate was measured by enzyme-linked immunosorbent assay (ELISA). For evaluation of the antibody activity of the conjugate, 5 ug collagen and 100 ul 0.1M sodium carbonate was placed in a microtiter well, followed sequentially by 1% bovine serum albumin, 0.25 ug conjugate or anticollagen, enzyme linked antiIgG (goat antimouse IgG labelled with alkaline phosphatase) from TAGO, and enzyme substrate (p-nitrophenyl phosphate). Qualitative evaluation of color provided evidence for a presence (yellow) or absence (clear) of enzyme and therefore of conjugate. Limit of detection was not investigated.

TEST EXAMPLE 1

In this example, the effectiveness of the conjugate to bind to posterior capsules and to inhibit growth of lens epithelial cells was determined by using bovine posterior capsules in vitro. Bovine posterior capsules, including the equatorial portions, were dissected from calf eyes obtained from a local slaughterhouse. Eyes were removed within one hour of slaughter and kept on ice until lens capsule removal, less than two hours thereafter. In determining whether the antibody would properly bind to bovine posterior lens capsules, the capsule was placed in a microtiter well and treated with 50 ul of solution containing 12.5 ug conjugate (or an equivalent amount of anticollagen or antialbumin or buffer). Following treatment, tissues were dried under vacuum (50 mtorr) at room temperature for three hours and fixed in ethanol for 15 minutes. Fixing in this manner eliminated false positives from untreated capsules, while retaining antibody activity of conjugate treated capsules. Assay by ELISA then continued as mentioned above.

Attachment of $^3$HMTX conjugate to bovine posterior capsules was studied in microtiter wells, similar to the first steps of ELISA. $^3$H conjugate (1500 dpm, or 830 dpm antialbumin conjugate, or 3900 dpm $^3$HMTX, or buffer) was incubated with the capsule for 60 minutes at room temperature. The capsule was rinsed, then homogenized in 5 ml Omnifluor and counted.

Tritium ($^3$H) incorporation indicated that 2.5 moles of MTX were bound to each mole of antibody. This corresponds to 3.9 ug MTX bound to 0.5 mg antibody. Pooled fractions with MTX activity had DHFR inhibition equivalent to 0.34 ug free MTX.

To determine the effect of the mitotic inhibitor on the remnant epithelial cells, the bovine posterior lens capsules, including the equatorial portions containing epithelial cells, were placed on glass slides and treated with 50 ul conjugate containing 0.15 ug bound MTX (or 2.5 ug MTX or buffer). These were incubated for two hours at 37 degrees in a humidified chamber. They were then transferred, without rinsing, to cell culture medium. Capsules were examined immediately to confirm presence of cells, incubated for seven days at 37 degrees, then reexamined for outgrowth.

Positive ELISA results were obtained after in vitro treatment of bovine posterior capsules with conjugate and with free anticollagen. Expected negative responses were obtained from antialbumin and buffer.

[3] Hconjugate treatment of bovine posterior capsule showed 59% attachment of label. $^3$HMTX and $^3$Hantialbumin conjugate attached less than 1%. In all cases, remaining activity was recovered in the rinsings.

Lens epithelia cells from bovine posterior capsules treated with conjugate did not grow. Cells treated with free MTX were only slightly inhibited compared to buffer treated cells, which grew well.

TEST EXAMPLE 2

In this in vivo example, five rabbits (six month old New Zealand white rabbits weighing 4.5 to 6.5 kg.) underwent bilateral extracapsular lens removal under general anesthesia. Lens material was aspirated/irrigated from the eye with BSS (Balanced Salt Solution obtained from Alcon labs), but no particular effort was made to remove epithelial cells at the lens equator. Each eye received a posterior chamber intraocular lens. Just before closure, 50 ul of solution containing 12.5 ug conjugate in which there was 0.15 ug MTX (or appropriate control) was injected into the anterior chamber, as summarized in Table 1. Eyes were treated externally with a broad spectrum antibiotic ointment after surgery and twice a day thereafter. After 48 hours, the animals were sacrificed by injection of an overdose of sodium pentobarbital. Posterior capsules, including ELISA, scintillation counting, or cell outgrowth, as with in vitro experiments of Test Example 1.

TABLE I

| Rabbit No. | Eye | Treatment | Assay |
|---|---|---|---|
| 1 | R | Anticollagen conjugate (12.5 ug) | ELISA |
| " | L | Anticollagen (12.5 ug) | " |
| 2 | R | Buffer | " |
| " | L | Antialbumin (12.5 ug) | " |
| 3 | R | $^3$HMTX anticollagen conjugate (1500 dpm) | $^3$H |
| " | L | $^3$HMTX antialbumin conjugate (830 dpm) | " |
| 4 | R | MTX (2.5 ug) | cell outgrowth |
| " | L | Anticollagen conjugate (12.5 ug, 0.15 ug MTX) | cell outgrowth |
| 5 | R | Anticollagen (12.5 ug) | cell outgrowth |
| " | L | Buffer | cell outgrowth |

TABLE I-continued

| Rabbit No. | Eye | Treatment | Assay |
|---|---|---|---|

Rabbit posterior capsules, after in vivo treatment, were placed directly into a cell culture medium to determine epithelial cell outgrowth. Capsules were examined immediately to confirm presence of cells, incubated for seven days at 37 degrees, then reexamined for outgrowth.

Using ELISA, both the conjugate and unconjugated anticollagen were found to be attached to the posterior capsule after 48 hours, while antialbumin and buffer controls gave a negative response.

Thirty percent of the radioactivity from the $^3$HMTX-anticollagen conjugate was recovered in the posterior capsule. This not only gives a quantitative measure of conjugate attachment, but also shows that the MTX remains conjugated to the antibody in vivo. An additional 8% was found in the cornea. No radioactivity above background was found in the eye treated with $^3$HMTX-antialbumin conjugate. The anticollagen conjugate completely inhibited cell outgrowth when the posterior capsule was placed in tissue culture medium. Free MTX (20 times the amount in the conjugate) and free anticollagen each depressed, but did not prevent, cell outgrowth. Good outgrowth was seen from the buffer treated capsule.

PREPARATION EXAMPLE 2

PMMA slides were plasma treated with ethylenediamine (EDAM) to yield chemically reactive amino groups available at the surface. These slides were further treated with gluteraldehyde (GA), rinsed of excess GA, and then treated with an MTX-protein conjugate. The conjugate was a covalent conjugate of MTX with bovine serum albumin, prepared using ECDI as the condensing agent, by the procedure of Kulkarni et al. cited above for preparing the MTX-antibody conjugate. Control slides were treated with unconjugated protein or MTX, respectively.

TEST EXAMPLE 3

The treated slides prepared in Preparation Example 2 above were evaluated for ability to support/inhibit outgrowth of lens epithelial cells from bovine anterior capsules. Outgrowth was followed for six days. Slides treated with the covalent conjugate of MTX inhibited cell outgrowth. When these slides were rinsed and evaluated again, they inhibited outgrowth for a second set of lens capsules. A third set of cells was somewhat inhibited, but not completely. This inhibition was not due to the gluteraldehyde, since the protein treated slide allowed good outgrowth. An MTX treated slide inhibited outgrowth during the first evaluation period, but not during subsequent evaluations.

The present invention may be embodied in other specific forms without departing from the spirit or the central attributes thereof and, accordingly, reference should be made to the appended claims, rather than to the foregoing specification as indicating the scope of the invention.

We claim:

1. A mitotic inhibitor for the prevention of posterior lens capsule opacification when instilled into the anterior or posterior chamber of the eye during or after extracapsular extraction comprising:

a conjugate of an anticollagen antibody and a cytotoxin to lens epithelial cells and fibroblasts.

2. A mitotic inhibitor according to claim 1 wherein said antibody and cytotoxin are covalently linked.

3. A mitotic inhibitor according to claim 1, wherein said cytotoxin comprises methotrexate.

4. A mitotic inhibitor according to claim 1, wherein said antibody is specific to lens capsule.

5. A mitotic inhibitor according to claim 1, wherein said antibody is specific to lens cells.

6. A mitotic inhibitor according to claim 1, wherein said conjugate comprises methotrexate and anticollagen in a molar ratio of about 1:1 to 10:1.

7. A method of preventing posterior lens capsule opacification after extracapsular cataract extraction comprising:

instilling into the anterior or posterior chamber of the eye during or after the extracapsular extraction the mitotic inhibitor of claim 1.

8. A method of preventing posterior lens capsule opacification after extracapsular cataract extraction comprising:

instilling the mitotic inhibitor of claim 1 immediately following the cataract extraction.

9. A method of preventing posterior lens capsule opacification after extracapsular cataract extraction comprising:

coating of intraocular lenses with the mitotic inhibitor of claim 1.

* * * * *